United States Patent
Munro

(10) Patent No.: US 9,050,396 B2
(45) Date of Patent: *Jun. 9, 2015

(54) DEVICE AND METHOD FOR BONE IMAGING

(75) Inventor: Chad Munro, Mabou (CA)

(73) Assignee: Halifax Biomedical Inc., Mabou, Nova Scotia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/203,263

(22) PCT Filed: Feb. 26, 2010

(86) PCT No.: PCT/CA2010/000273
§ 371 (c)(1),
(2), (4) Date: Sep. 22, 2011

(87) PCT Pub. No.: WO2010/096927
PCT Pub. Date: Sep. 2, 2010

(65) Prior Publication Data
US 2012/0004536 A1    Jan. 5, 2012

Related U.S. Application Data

(60) Provisional application No. 61/202,433, filed on Feb. 27, 2009.

(51) Int. Cl.
*A61B 5/103* (2006.01)
*A61L 31/18* (2006.01)
*A61B 6/12* (2006.01)
*A61B 19/00* (2006.01)

(52) U.S. Cl.
CPC ............ *A61L 31/18* (2013.01); *A61B 6/12* (2013.01);*A61B 19/54* (2013.01); *A61B 2019/5416* ; (2013.01); *A61F 2250/0032* (2013.01); *A61F 2250/0098* (2013.01); *A61L 2430/02* (2013.01)

(58) Field of Classification Search
CPC ...... A61B 5/4504; A61B 5/076; A61B 5/103; A61B 5/1121; A61B 5/1127; A61B 19/54; A61F 2002/4666
USPC ......................................... 600/426, 431, 420
See application file for complete search history.

(56) References Cited

U.S. PATENT DOCUMENTS

| | | |
|---|---|---|
| 7,488,343 B2 | 2/2009 | O'Brien et al. |
| 7,491,179 B2 | 2/2009 | Roy et al. |
| 2003/0040806 A1 | 2/2003 | MacDonald |
| 2007/0270851 A1* | 11/2007 | Erickson et al. ................ 606/69 |
| 2008/0161729 A1 | 7/2008 | Bush |
| 2008/0269898 A1 | 10/2008 | Carls et al. |
| 2008/0294258 A1 | 11/2008 | Revie et al. |

FOREIGN PATENT DOCUMENTS

| | | |
|---|---|---|
| CA | 2446573 | 3/1998 |
| CA | 2238784 | 2/1999 |
| CA | 2427767 | 5/2003 |
| CA | 2485013 | 11/2003 |
| CA | 2536947 | 3/2005 |
| CA | 2679691 | 9/2008 |

\* cited by examiner

*Primary Examiner* — Elmer Chao
(74) *Attorney, Agent, or Firm* — Gowling Lafleur Henderson LLP

(57) ABSTRACT

The invention comprises a modified implant useful to assess bone by imaging. The modified implant comprises a medical implant and at least one detectable marker element associated with the implant that serves as a reference point in medical imaging. Preferably, the implant and the detector marker elements have different radiolucencies such that one element can be seen through the other in medical imaging.

2 Claims, 1 Drawing Sheet

DEVICE AND METHOD FOR BONE IMAGING

FIELD OF INVENTION

The present invention relates to medical devices, and in particular, a medical implant that is useful in bone imaging to track bone growth, healing and motion.

BACKGROUND OF THE INVENTION

Medical implants are frequently used to support bones during healing. However, assessment of healing is difficult. Diagnostic techniques such as MRI or CT do not have sufficient resolution to determine if healing has occurred.

The current standard for the assessment of fracture healing is a planar radiograph and the current standard for assessment of spinal fusion for example is direct palpation of the spine in a second exploratory operation. Flexion extension comparisons using MRI have reported accuracy of 5 degrees which is not sufficient for the determination of fusion.

Thus, there exists a need to establish a method and device that provides assessment of fusion and bone healing. Having the ability to assess bone healing would assist surgeons in clinical decision-making regarding the treatment of patients, such as whether to apply or avoid surgical intervention.

SUMMARY OF THE INVENTION

The present invention addresses the need for an improved method of assessing bone.

In one aspect of the invention, there is provided a modified implant comprising:
  i) a medical implant; and
  ii) at least one detectable marker element associated with the implant that can serve as a reference point in medical imaging.

In a preferred embodiment, the implant and the detectable marker element have different radiolucencies such that the detectable marker element can be seen through the implant in medical imaging.

In a further preferred embodiment, the implant comprises titanium and the detectable marker comprises tantalum.

In another embodiment of the invention, the detectable marker comprises a void in the implant.

The modified implant preferably comprises a detectable marker that is spherical in shape.

In yet another embodiment of the invention, the modified implant has a unique outer geometry that acts as a detectable marker such that the position of the implant can be precisely established by medical imaging.

In a further preferred embodiment, the modified implant comprises a radio-opaque substance applied to one or both ends of the implant as the detectable marker.

In another aspect of the invention, a method of assessing bone is provided. The method comprises the steps of:
  i. implanting a modified implant into a portion of bone adjacent to a target site;
  ii. determining the position of the modified implant through medical imaging;
  iii. applying load to the bone;
  iv. determining the position of the implant under load bearing conditions;
  v. comparing the position of the modified implant in an unloaded state with the position of the modified implant under load bearing conditions; and
  vi. determining the distance the modified implant moved;

wherein the less the difference in position of the implant in the unloaded state as compared to the load-bearing state, the better the assessment.

In a preferred embodiment of this method, a modified implant is implanted into the bone on each side of a target site and the distance between the modified implants under unloaded and loaded conditions is determined.

BRIEF DESCRIPTION OF THE DRAWINGS

These and other features of the invention will become more apparent from the following description in which reference is made to the appended drawings wherein.

DETAILED DESCRIPTION

The invention relates to modified medical implants that can be used in bone assessment. The modified implant includes an implant modified with a detectable marker that can readily be detected to determine the position of the modified implant.

The term "bone assessment" is used herein to encompass the assessment of bone healing following injury by fracture or surgical intervention that create the same biological conditions as an injury, assessment of surgical fusions such as spine and ankle fusion operations, the assessment of bone growth and bone motion for any other reason.

In one aspect of the invention, medical implants comprising small radio-opaque elements as the detectable marker are provided in which these elements are embedded or attached to the medical implant. These elements are more radio-opaque than the medical implant itself. The result is that in an x-ray of the implant/bone construct, the embedded elements can be clearly seen. The embedded elements are preferably in the shape of a sphere since this shape is readily detected as a point in an X-ray. Comparisons between a loaded state of an implant/bone construct may be compared to an unloaded state of the same region. The embedded elements may be used as precise reference points on medical images. The relative motion of the embedded elements across a target bone zone when a load is applied is a representative measure of the stiffness of that zone and, thus, is useful to assess the bone. For example, with respect to bone healing, as a bone heals, the bone healing zone stiffness will approach the stiffness of healthy bone.

Figure 1:
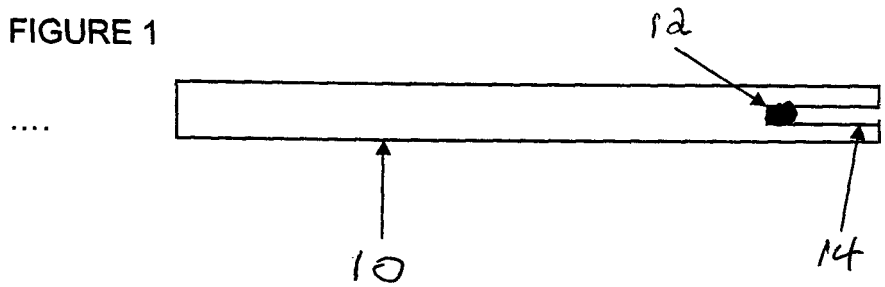
FIG. 1 is an illustration of one embodiment of a modified implant device in accordance with the invention.

FIG. 1 illustrates a medical implant 10 that can be associated with a bone to be assessed, e.g. a bone that is undergoing healing. In this embodiment, the implant device includes an embedded element 12 that has a different radiolucency than that medical implant. The embedded element is shown as press-fitted into a channel 14 that is machined into the implant.

In one preferred embodiment, the medical implant is made of titanium and the embedded element is a tantalum sphere.

Figure 2:
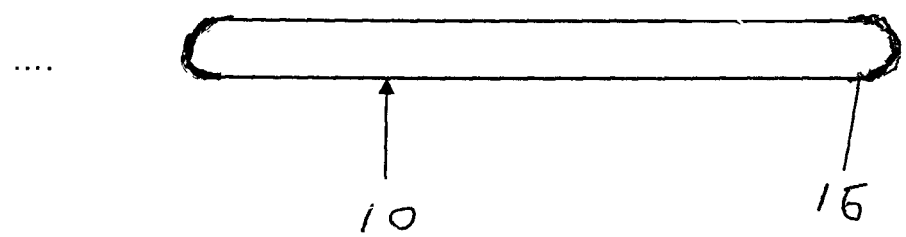
FIG. 2 is an illustration of another embodiment of a modified implant device in accordance with the invention.

In another embodiment, the shape of the medical implant is modified such that partial spheres 16 are clearly visible in the implant contour as shown in FIG. 2. At least one end of the implant may have a curved (half sphere) contour 16 that is embedded with a radio-opaque element as a detectable marker. The position of the implant end can be measured as described above by imaging of the embedded element. In this case, even without having a more radio-opaque element associated with the implant, the modified shape alone can act as a reference point for the purposes of assessing bone.

Figure 3:
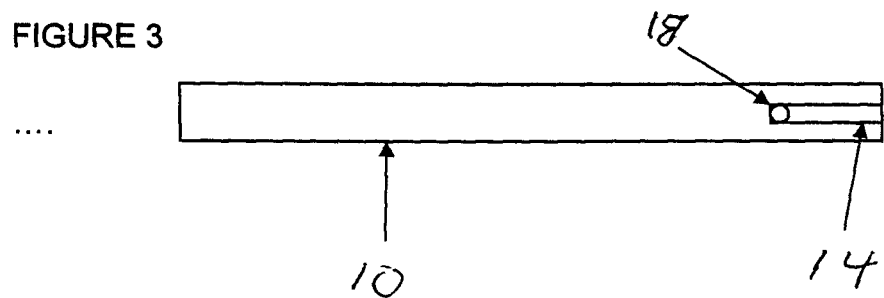
FIG. 3 is an illustration of a further embodiment of a modified implant device in accordance with the invention.

In another embodiment of the device, the detectable marker is in the shape of machined voids or cavities 18 in the medical implant 10 as shown by the empty sphere in FIG. 3. Such empty spheres, which may include air or bodily fluids, provide sufficient differences in radiolucency that the position of the void can be precisely determined by imaging.

In use, a modified implant according to the invention is implanted in the bone adjacent to a target site, such as damaged bone. A baseline measurement is taken, load is applied to the bone and the distance of travel of the modified implant is measured. Preferably a modified implant is implanted on each side of the target site. A baseline measurement indicating the distance between the detectable markers on each implant in an unloaded state is recorded and compared to the distance between the two markers under a loaded state. The relative distance between the markers is recorded and this distance is an indicator of rigidity in the bone and thus enables assessment of bone, for example, assessment of bone healing.

As will be appreciated by one of skill in the art, the present modified implant is useful to track any motion of a bone in the body under loaded conditions or under dynamic x-ray acquisition. For example, the implant may be in the form of a pedical screw for a device that is designed to preserve the motion of the spine. In this case, detectable marker embedded within the screw implant may be used to track the motion of bone segments under dynamic imaging modalities such as fluoroscopic, stereo fluoroscopic, dynamic DR imaging or stereo DR imaging.

Specific detectable markers, such as an embedded sphere of radio-opaque material, the insertion of a radio-opaque element at a specific site on the implant, the shape of the implant itself, and a cavity with or without air have been described above. It is clearly apparent however that any type of detectable marker that indicates the position of the modified implant may be used in the devices and methods of the invention.

I claim:

1. A method of assessing a bone, said method comprising the steps of:
   i) implanting into a bone adjacent to a target site, a first bone assessment device comprising (a) an elongate rigid implant for implantation into a bone for assessment of bone fusion and healing, said implant having a first radiolucency detectable with medical imaging, and (b) a marker element associated with the implant, said marker element having a second radiolucency detectable with medical imaging;
   ii) determining the position of the first bone assessment device by establishing the position of the detectable marker element with medical imaging as a first reference point;
   iii) applying a load to the bone;
   iv) determining the position of the first bone assessment device under load bearing conditions by establishing the position of the detectable marker element with medical imaging as a second reference point; and
   v) determining the distance between the first reference point and the second reference point;
   wherein a lesser difference in position of the first bone assessment device in the unloaded state as compared to the load-bearing state, is an indicator of bone rigidity.

2. The method according to claim 1 wherein the first bone assessment device is inserted into the bone on one side of a target site and a second bone assessment device is inserted into the bone on the other side of the target site and the distance between the first reference point and the second reference point is determined.

* * * * *